(12) United States Patent
Li et al.

(10) Patent No.: US 9,675,117 B2
(45) Date of Patent: Jun. 13, 2017

(54) ATOMIZER FOR ELECTRONIC CIGARETTE AND ELECTRONIC CIGARETTE HAVING THE SAME

(71) Applicant: Shenzhen First Union Technology Co., Ltd., Shenzhen (CN)

(72) Inventors: Yonghai Li, Shenzhen (CN); Zhongli Xu, Shenzhen (CN); Hepeng Hong, Shenzhen (CN); Laizhi Song, Shenzhen (CN); Xingbing Zou, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 637 days.

(21) Appl. No.: 14/152,572

(22) Filed: Jan. 10, 2014

(65) Prior Publication Data

US 2014/0190503 A1 Jul. 10, 2014

(30) Foreign Application Priority Data

Jan. 10, 2013 (CN) .......................... 2013 1 0009089
May 29, 2013 (CN) .......................... 2013 1 0205022

(51) Int. Cl.
*A24F 47/00* (2006.01)
*A61M 15/06* (2006.01)
*A61M 11/04* (2006.01)

(52) U.S. Cl.
CPC ......... *A24F 47/008* (2013.01); *A61M 11/044* (2014.02); *A61M 15/06* (2013.01); *A61M 2205/3653* (2013.01); *A61M 2205/8206* (2013.01)

(58) Field of Classification Search
CPC .............................. A24F 47/008; A61M 15/06
See application file for complete search history.

(56) References Cited

U.S. PATENT DOCUMENTS

| | | | |
|---|---|---|---|
| 2014/0060554 A1* | 3/2014 | Collett | H05B 3/265 131/328 |
| 2014/0123989 A1* | 5/2014 | Lamothe | A24F 47/008 131/328 |
| 2015/0047662 A1* | 2/2015 | Hopps | A24F 47/008 131/329 |

FOREIGN PATENT DOCUMENTS

| | | |
|---|---|---|
| CN | 201986689 | 9/2011 |
| CN | 202445135 | 9/2012 |
| CN | 202603608 | 12/2012 |
| CN | 103054196 | 4/2013 |

(Continued)

*Primary Examiner* — Cynthia Szewczyk
(74) *Attorney, Agent, or Firm* — Hamre, Schumann, Mueller & Larson, P.C.

(57) ABSTRACT

An exemplary atomizer includes a mouthpiece assembly, two heating assemblies, a fixing assembly, an atomizing sleeve, a switching assembly. The two heating assemblies are configured for heating and atomizing oils of two different tastes respectively. One end of each heating assembly is engaged with the mouthpiece assembly. The fixing assembly is hermetically coupled to the mouthpiece assembly, and is configured for securing the two heating assemblies. The atomizing sleeve is hermetically connected to the fixing assembly, with the two heating assemblies nested therein. The switching assembly is coupled to ends of the two heating assemblies away from the mouthpiece assembly. The switching assembly is configured for enabling one of two heating assemblies selectively.

18 Claims, 9 Drawing Sheets

(56) References Cited

FOREIGN PATENT DOCUMENTS

CN 203072894 7/2013

* cited by examiner

ÄTOMIZER FOR ELECTRONIC CIGARETTE AND ELECTRONIC CIGARETTE HAVING THE SAME

TECHNICAL FIELD

The present invention relates to electronic cigarettes, and particularly to an atomizer and an electronic cigarette using same.

BACKGROUND ART

Electronic cigarettes are similar to conventional cigarettes in appearance and taste, but less harmful to human's health, such that electronic cigarettes are widely used for helping people to quit smoke. A typical electronic cigarette has only one heating assembly, accordingly can only provide smoke of one taste, and when one heating component is damaged, then the entire electronic cigarette cannot be used. The smoker may get tired of the single taste of smoke after using the electronic cigarette for a long time.

What is needed, therefore, is an atomizer and an electronic cigarette using same, which can overcome the above shortcomings.

SUMMARY OF THE INVENTION

An exemplary atomizer includes a mouthpiece assembly, two heating assemblies, a fixing assembly, an atomizing sleeve, a switching assembly. The two heating assemblies are configured for heating and atomizing oils of two different tastes respectively. One end of each heating assembly is engaged with the mouthpiece assembly. The fixing assembly is hermetically coupled to the mouthpiece assembly, and is configured for securing the two heating assemblies. The atomizing sleeve is hermetically connected to the fixing assembly, with the two heating assemblies nested therein. The switching assembly is coupled to ends of the two heating assemblies away from the mouthpiece assembly. The switching assembly is configured for enabling one of two heating assemblies selectively.

BRIEF DESCRIPTION OF THE DRAWINGS

Many aspects of the present atomizer and electronic cigarette can be better understood with reference to the following drawings. The components in the drawings are not necessarily drawn to scale, the emphasis instead being placed upon clearly illustrating the principles of the present atomizer and electronic cigarette. Moreover, in the drawings, like reference numerals designate corresponding parts throughout the several views.

DETAILED DESCRIPTION

Embodiments of the present atomizer and electronic cigarette will now be described in detail below and with references to the drawings.

Figure 1:
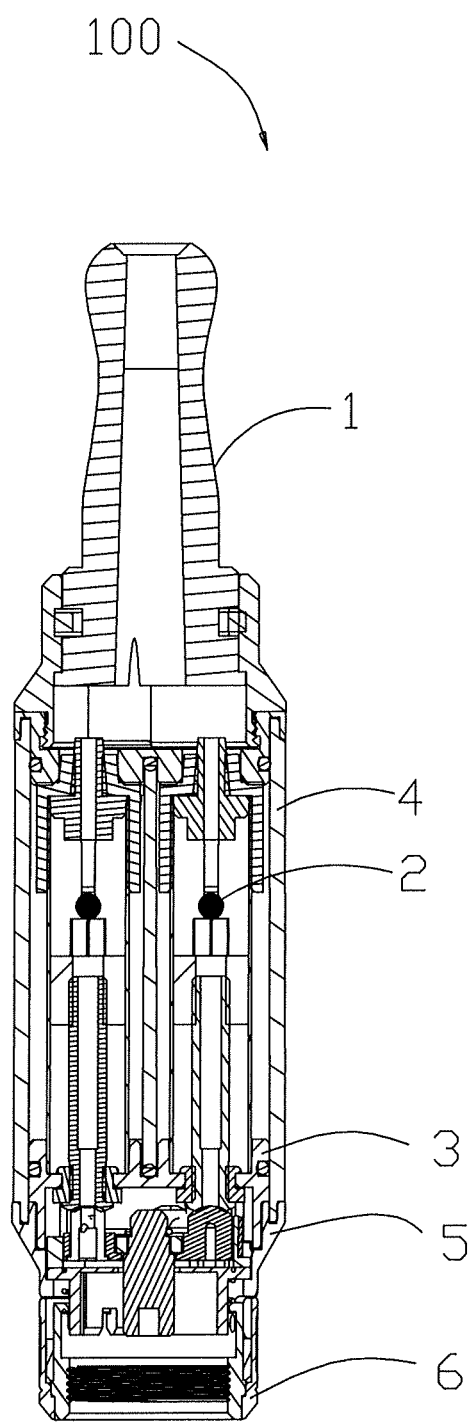
FIG. 1 is a cross-sectional view of an atomizer according to a first embodiment.

Referring to FIG. 1, an atomizer 100 for electronic cigarette according to a first embodiment, mainly includes a mouthpiece assembly 1, two heating assemblies 2, a fixing assembly 3, an atomizing sleeve 4, and a switching assembly 5.

One end of each heating assembly 2 is engaged with the mouthpiece assembly 1. The two heating assemblies 2 are configured (i.e., structured and arranged) for heating and atomizing oils of different tastes. The fixing assembly 3 is hermetically coupled to the mouthpiece assembly 1, and configured for securing the two heating assemblies 2. The atomizing sleeve 4 is hermetically coupled to the fixing assembly 3, with the two heating assemblies 2 received therein. Ends of the two heating assemblies 2 away from the mouthpiece assembly 1, are connected to the switching assembly 5. The switching assembly 5 is adapted for enabling (i.e., powering on) one of two heating assemblies selectively. The atomizing sleeve 4 can be made of organic glass, crystal, or other materials of high transparency.

Figure 3:
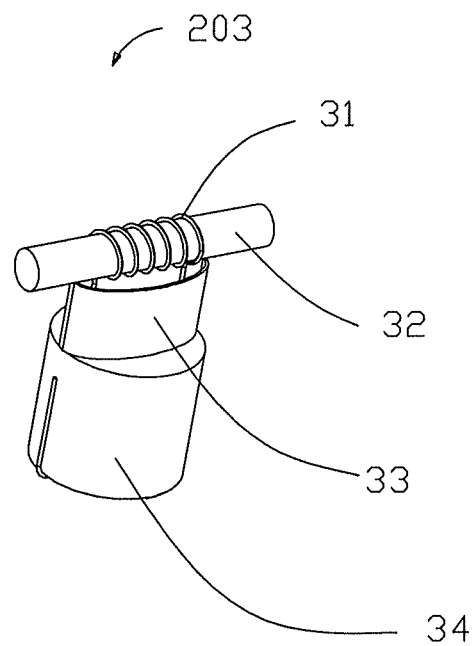
FIG. 3 is an isometric view of a heating wire component of the heating assembly of FIG. 2.

Referring also to FIG. 3, the mouthpiece assembly 1 includes a mouthpiece 101, and a fixture 103. The mouthpiece 101 is mounted on the fixture 103 via a latch 102. The mouthpiece 101 defines two through holes 104. The mouthpiece 101 may be soft or hard. The two heating assemblies 2 are coupled to the two through holes 104 respectively via seal sleeves 105. The position between the heating assemblies 2 and the through holes 104 is fixed.

The fixing assembly 3 includes an upper holder 301 and a lower holder 302. One end of the upper holder 301 is connected to the fixture 103, and the other end of the upper holder 301 is connected to one end of the atomizing sleeve 4 by a seal ring 303. In the present embodiment, the upper holder 301 is threadedly coupled to the atomizing sleeve 4. One end of the lower holder 302 is hermetically connected to the other end of the atomizing sleeve 4, the other end of the lower holder 302 is connected to the switching assembly 5. The lower holder 302 defines two through holes 304, so that each heating assembly 2 can extend through the through holes 304 to be electrically connected to the switching assembly 5.

Figure 2:
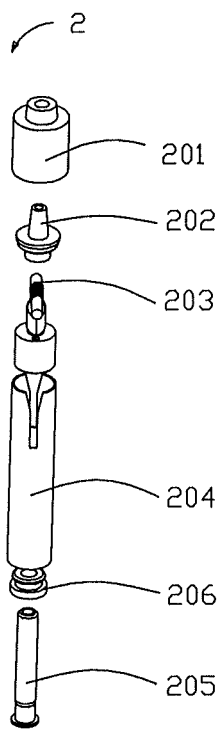
FIG. 2 is an exploded isometric view of a heating assembly of the atomizer of FIG. 1.

Referring to FIG. 2, each heating assembly 2 sequentially includes a mouthpiece seal sleeve 201, a mouthpiece seal gaskets 202, a heating wire component 203, an air pipe 204, a tubular electrode 205, and an insulative ring 206. The air pipe 204 is configured for supporting the heating wire component 203, and providing an air passage. The insulative ring 206 is disposed between the tubular electrode 205 and the air pipe 204, so that the tubular electrode 205 is insulative from the air pipe 204. The heating assembly 2 is hermetically connected to the through hole 104 of the mouthpiece assembly 1 via the mouthpiece 201. The air tube 204, the atomizing sleeve 4, the upper holder 301 and the lower holder 302 cooperatively form a sealed space as an oil reserving chamber. The atomizing sleeve 4 includes a spacer, which divides the oil reserving chamber into two separate sub-chambers for reserving oils of different tastes. Each heating assembly 2 is configured for heating oil of a sub-chamber.

The air tube 204 is connected to a negative electrode of a battery. The tubular electrode 205 is connected to a positive electrode of the battery.

Referring to FIG. 3, the heating wire component 203 includes a heating wire 31, a glass fiber core 32, a glass fiber tube 33, and a silicon base 34. The heating wire 31 is wound around the glass fiber core 32. Two ends of the heating wire 31 are connected to the positive and negative electrodes of the battery, respectively. In this way, the heating wire 31 is heated.

Figure 4:
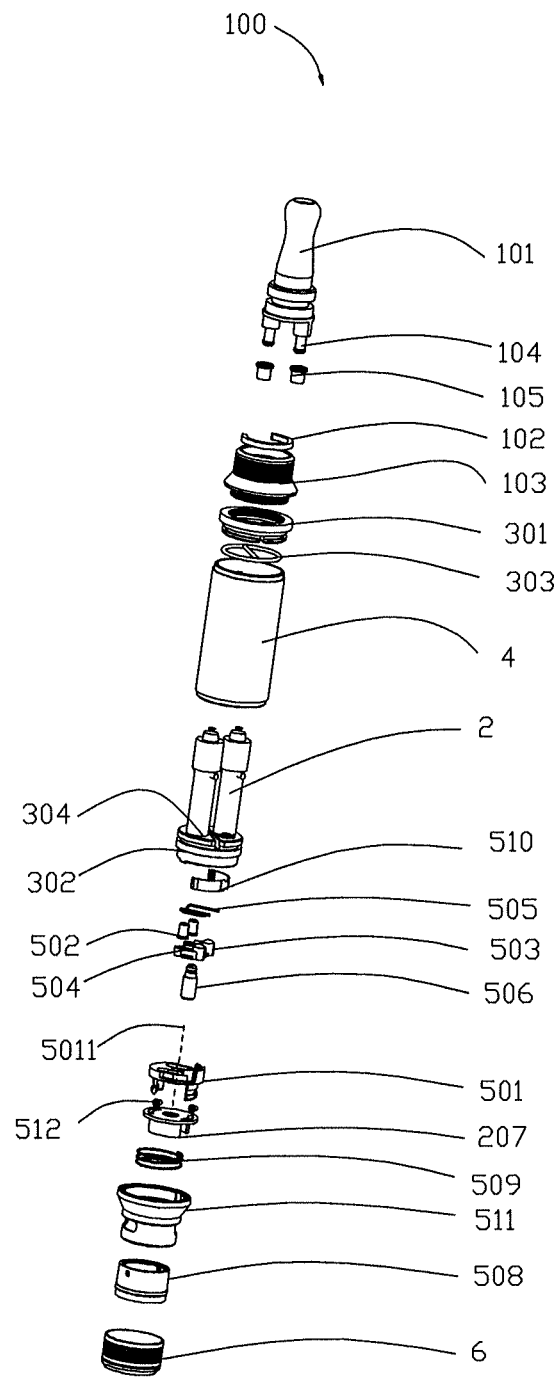
FIG. 4 is an exploded isometric view of the atomizer of FIG. 1.
Figure 5:
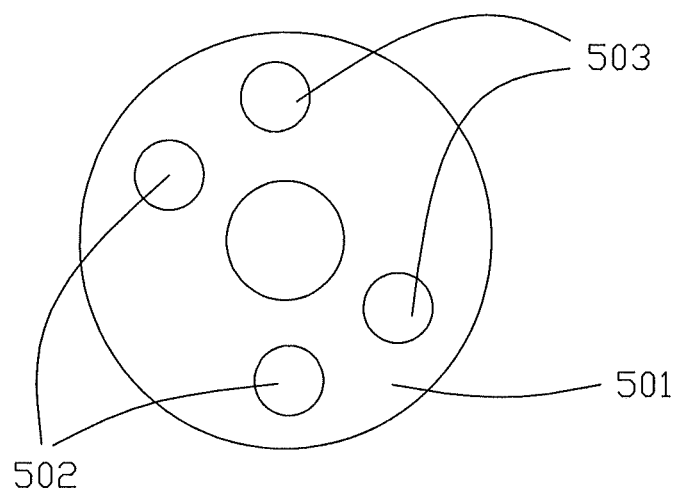
FIG. 5 is a schematic plan view showing a spatial relationship among a rotary table, two positive beads, and two insulative beads of the atomizer of FIG. 1.

Referring to FIGS. 4-5, the switching assembly 5 mainly includes a rotary table 501, two positive beads 502, two insulative beads 503, a seat 504, a positive spring 505, a positive cylindrical electrode 506, a shielding plate 507, a screwed sleeve 508, a negative spring 509, an elastic plate 510, a switching base 511, and two pins 512. The positive beads 502 and the insulative beads 503 are arranged on the seat 504. The seat 504 is fixed on the rotary table 501. The positive cylindrical electrode 506 is fixed at a center of the rotary table 501, and is electrically connected to the positive beads 502. The shielding plate 507 is for shielding internal components, so that internal structure of the switching assembly 5 looks simple. The screwed sleeve 508 is fixed with the rotary table 501, electrically connected to the negative electrode of the battery, and is configured for threadedly coupling to a battery assembly (not shown). The negative spring 509 is electrically connected to the screwed sleeve 508 and the switching base 511, and makes sure reliability of connection to the negative electrode. The switching base 511 is fixedly coupled to the fixing assembly 3. The elastic plate 510 is engaged with the lower holder 302. The rotary table 501 is rotatable around a central axis 5011 thereof relative the switching base 511. The positive cylindrical electrode 506 is connected to the positive electrode of the battery.

Each positive bead 502 is corresponding to an insulative bead 503. Each positive bead 502 and a corresponding insulative bead 503 are arranged spatially corresponding to the two heating assemblies 2. When one heating assembly 2 aligns with one of the positive beads 502 and electrically contacts the one of the positive beads 502, the other heating assembly 2 aligns with the other of the insulative beads 503, contacts the other of the insulative beads 503, and is disconnected from the positive electrode of the battery. A central axis of each positive bead 502 and a central axis of a corresponding insulative bead 503 are symmetric about the central axis 5011 of the rotary table 501. The two positive beads 502 and the two insulative beads 503 are arranged in a circle centered at a center of the rotary table 501. A distance between each positive bead 502 and the corresponding insulative bead 503 is substantially equal to that between the two heating assemblies 2. At one time, only one heating assembly 2 is powered on, and accordingly, oil of only one taste is heated and atomized.

The rotary table 501 is capable of rotating between a first position and a second position. When the rotary table 501 is in the first position, one heating assembly 2 is in contact with one of the positive beads 502, and is powered on; when the rotary table 501 is in the second position, the other heating assembly 2 is in contact with the other of the positive beads 502, and is powered on.

The shielding plate 507 is fixed on the rotary table 501 through pins 512. The positive cylindrical electrode 506 is fixed at the center of the rotary table 501, and is clamped by the positive spring 505.

The atomizer 100 further includes an ornament ring 6 engaged with the switching base 511 for indicating information about smoke of current taste provided by the atomizer 100.

In the present embodiment, the atomizer 100 includes two heating assemblies 2, and the switching assembly 5. The switching assembly 5 enables one of the two heating assemblies 2 selectively, thereby heating and atomizing oil of desired taste. Accordingly, it is very convenient for the smoker to enjoy smoke of different tastes.

It is to be understood that in other embodiments, the two heating assemblies 2 may be configured for heating and atomizing oil of identical taste.

Figure 6:
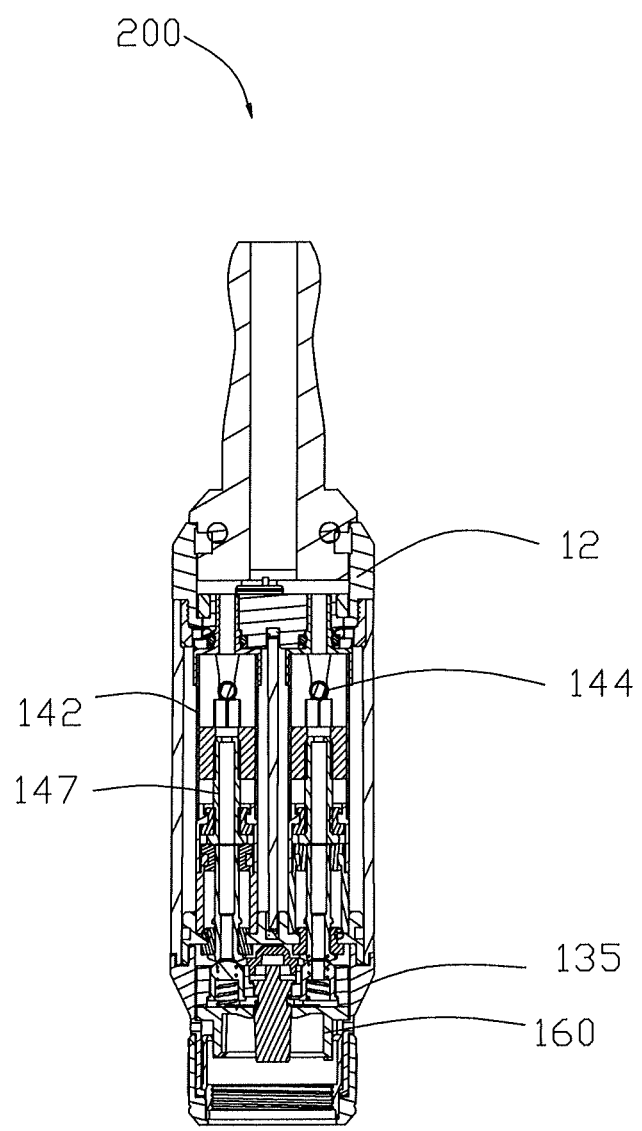
FIG. 6 is a cross sectional view of an atomizer according to a second embodiment, taken along a surface passing a central axis thereof.
Figure 7:
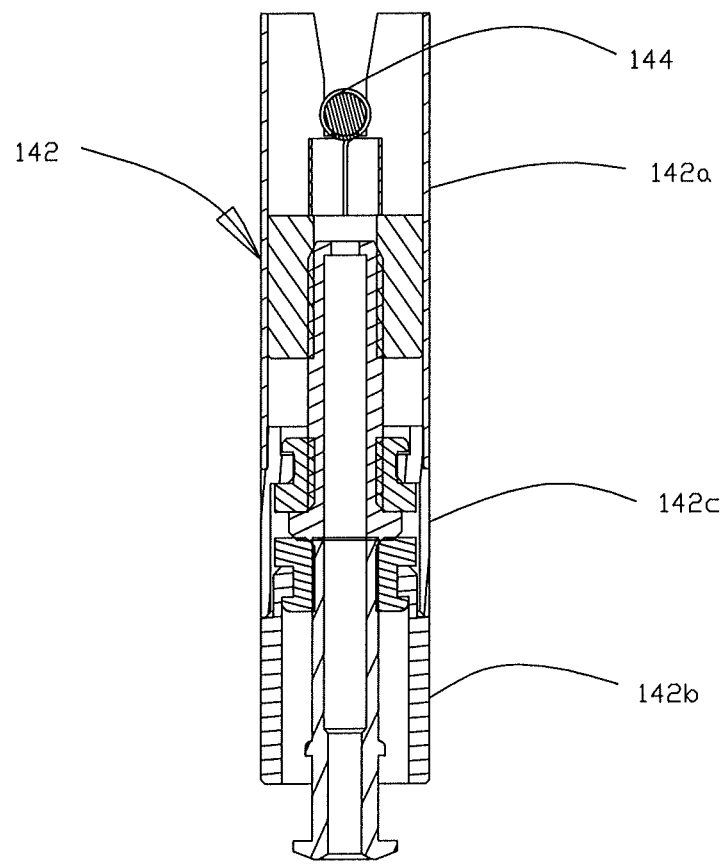
FIG. 7 is a schematic view of an air tube and internal components in the air tube of FIG. 2.
Figure 8:
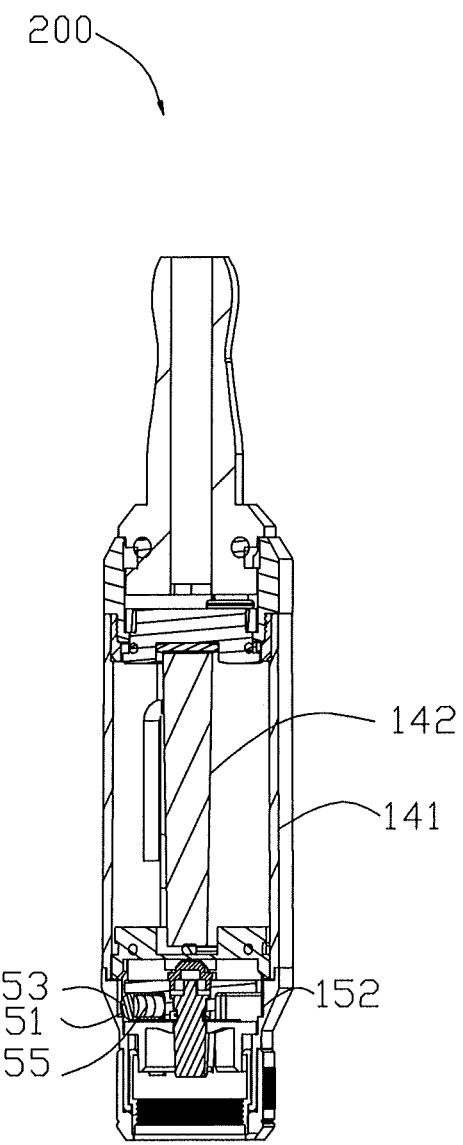
FIG. 8 is another cross sectional view of atomizer of FIG. 1 taken along another surface passing the central axis.

Referring to FIGS. 6-8, an atomizer 200 according to a second embodiment is shown. Since the atomizer 200 is similar to the atomizer 100, similar structures will not be described for brevity.

The atomizer 200 includes two air pipes 142, an upper holder 12, two tubular electrode 147, two heating wires 144, a shifting base 135, a rotary table 160, a spring 155, and an engaging portion 153.

The upper holder 12 defines two fixing holes 121. The two air pipes 142 are detachably coupled in the two fixing holes 121 accordingly.

In the present embodiment, each air pipe 142 includes a first part 142a, a second part 142b, and a middle part 142c detachably interconnected between the first part 142a and the second part 142b. One end of the first part 142a is detachably coupled to the fixing hole 121. Accordingly, when the tubular electrode 147 is damaged due to high temperature of the heating wires 144, the first part 142a, the tubular electrode 147 and the heating wires can be removed and replaced. The air pipe 142 includes several parts (i.e., the first part 142a, etc.), so that it is convenient to replace part of the air pipe 142 and internal components (e.g., the tubular electrode 147) within the air pipe 142, without replacing the whole air pipe 142, thereby reducing cost.

The shifting base 135 defines a first recess 151 and a second recess 152 in an inner surface thereof. The first and second recesses 151, 152 are arc-shaped in cross-section. The spring 155 is connected to one end of the engaging portion 153. The engaging portion 153 is slidable along a longitudinal direction of the spring 155 on the rotary table 160. One end of the engaging portion 153 away from the spring 155 is also arc-shaped in cross-section, so that the engaging portion 153 matches with the first and second recesses 152.

In a first position, the engaging portion 153 is pushed by the spring 155 to snapingly engage into the first recess 151, and oil of a first taste is heated and atomized. When the rotary table 160 is rotated to a second position, the engaging portion 153 is pushed by the spring 155 to snapingly engage into the second recess 152, and oil of a second taste is heated and atomized. The rotary table 160 and the engaging portion 153 make it convenient for the smoker to shift taste of the atomizer 134.

In other embodiments, the atomizer 200 may include two engaging portions 153, which insert into the first and second recesses 151, 152, respectively.

Figure 9:
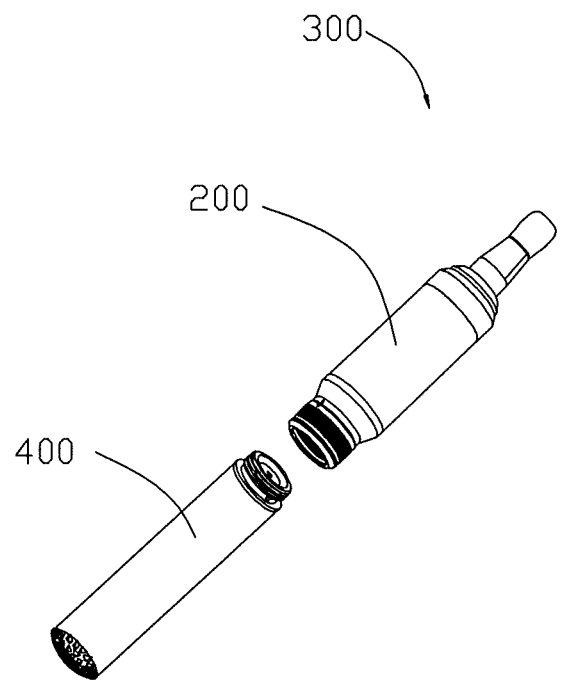
FIG. 9 is a partly exploded isometric view of an electronic cigarette according to a third embodiment.

Referring to FIG. 9, an electronic cigarette 300 according to a third embodiment includes the atomizer 200 and a battery assembly 400. The battery assembly 400 is threadedly coupled to one end of the atomizer 200. The electronic cigarette 300 can provide the smoker two different taste of smoke. It should be understood that the atomizer 200 can be replaced by the atomizer 100 of FIG. 1.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for electronic cigarette, comprising:
   a mouthpiece assembly;
   two heating assemblies configured for heating and atomizing oils of two different tastes respectively, one end of each heating assembly being engaged with the mouthpiece assembly;
   a fixing assembly hermetically coupled to the mouthpiece assembly, the fixing assembly being configured for securing the two heating assemblies;
   an atomizing sleeve hermetically connected to the fixing assembly, and nesting the two heating assemblies therein; and
   a switching assembly coupled to ends of the two heating assemblies away from the mouthpiece assembly, the switching assembly being configured for enabling one of two heating assemblies selectively,
   wherein the switching assembly comprises
      a rotary table;
      two positive beads electrically connected to a positive electrode of a battery; and
      two insulative beads,
      wherein the rotary table is rotatable relative to the fixing assembly around a central axis thereof;
         each positive bead is corresponding to an insulative bead;
         each positive bead and a corresponding insulative bead are arranged spatially corresponding to the two heating assemblies;
         when one heating assembly aligns with one of the positive beads and electrically contacts the one of the positive beads, the other heating assembly aligns with the other of the insulative beads, contacts the other of the insulative beads, and is disconnected from the positive electrode;
         the rotary table is capable of rotating between a first position and a second position;
         when the rotary table is in the first position, one heating assembly is in contact with one of the positive beads, and is powered on; and
         when the rotary table is in the second position, the other heating assembly is in contact with the other of the positive beads, and is powered on.

2. The atomizer of claim 1, wherein the fixing assembly comprises an upper holder, the upper holder is hermetically coupled to the mouthpiece assembly, the two heating assemblies each comprise an air tube, the upper holder defines two fixing holes therein, and the two air pipes are detachably coupled in the two fixing holes respectively.

3. The atomizer of claim 2, wherein each air pipe comprises a first part, a second part, and a middle part detachably interconnected between the first part and the second part, one end of the first part is detachably coupled to the fixing hole.

4. The atomizer of claim 1, wherein a distance between each positive bead and the corresponding insulative bead is substantially equal to that between the two heating assemblies.

5. The atomizer of claim 1, wherein the switching assembly further comprises a switching base, a screwed sleeve, the switching base is fixedly coupled to the fixing assembly, the screwed sleeve is fixed with the rotary table, and is configured for threadedly coupling to a battery assembly.

6. The atomizer of claim 5, wherein the switching assembly further comprises a spring and an engaging portion, the spring is connected to one end of the engaging portion, the engaging portion is slidable along a longitudinal direction of the spring on the rotary table, the shifting base defines a first recess and a second recess in an inner surface thereof, when the rotary table is in a first position, the engaging portion is pushed by the spring to engage into the first recess, and oil of a first taste is heated and atomized; when the rotary table is rotated to a second position, the engaging portion is pushed by the spring to engage into the second recess, and oil of a second taste is heated and atomized.

7. The atomizer of claim 5, wherein the switching assembly further comprises an ornament ring engaged with the switching base for indicating information about smoke of current taste provided by the atomizer.

8. An electronic cigarette, comprising:
   an atomizer according to claim 1; and
   a battery assembly configured for providing the atomizer power.

9. The electronic cigarette of claim 8, wherein the fixing assembly comprises an upper holder, the upper holder is hermetically coupled to the mouthpiece assembly, the two heating assemblies each comprise an air tube, the upper holder defines two fixing holes therein, and the two air pipes are detachably coupled in the two fixing holes respectively.

10. The electronic cigarette of claim 9, wherein each air pipe comprises a first part, a second part, and a middle part detachably interconnected between the first part and the second part, one end of the first part is detachably coupled to the fixing hole.

11. The electronic cigarette of claim 8, wherein a distance between each positive bead and the corresponding insulative bead is substantially equal to that between the two heating assemblies.

12. The electronic cigarette of claim 8, wherein the switching assembly further comprises a switching base, a screwed sleeve, the switching base is fixedly coupled to the fixing assembly, the screwed sleeve is fixed with the rotary table, and is configured for threadedly coupling to a battery assembly.

13. The electronic cigarette of claim 12, wherein the switching assembly further comprises a spring and an engaging portion, the spring is connected to one end of the engaging portion, the engaging portion is slidable along a longitudinal direction of the spring on the rotary table, the shifting base defines a first recess and a second recess in an inner surface thereof, when the rotary table is in a first position, the engaging portion is pushed by the spring to engage into the first recess, and oil of a first taste is heated and atomized; when the rotary table is rotated to a second position, the engaging portion is pushed by the spring to engage into the second recess, and oil of a second taste is heated and atomized.

14. The electronic cigarette of claim 12, wherein the switching assembly further comprises an ornament ring engaged with the switching base for indicating information about smoke of current taste provided by the atomizer.

15. An atomizer for electronic cigarette, comprising:
    a mouthpiece assembly;

two heating assemblies configured for heating and atomizing oil, one end of each heating assembly being engaged with the mouthpiece assembly;

a fixing assembly hermetically coupled to the mouthpiece assembly, the fixing assembly being configured for securing the two heating assemblies;

an atomizing sleeve hermetically connected to the fixing assembly, and nesting the two heating assemblies therein; and a switching assembly coupled to ends of the two heating assemblies away from the mouthpiece assembly, the switching assembly being configured for enabling one of two heating assemblies selectively, wherein the switching assembly comprises
a rotary table;
two positive beads electrically connected to a positive electrode of a battery; and
two insulative beads,
wherein the rotary table is rotatable relative to the fixing assembly around a central axis thereof;
each positive bead is corresponding to an insulative bead;
each positive bead and a corresponding insulative bead are arranged spatially corresponding to the two heating assemblies;
when one heating assembly aligns with one of the positive beads and electrically contacts the one of the positive beads, the other heating assembly aligns with the other of the insulative beads, contacts the other of the insulative beads, and is disconnected from the positive electrode;
the rotary table is capable of rotating between a first position and a second position;
when the rotary table is in the first position, one heating assembly is in contact with one of the positive beads, and is powered on; and
when the rotary table is in the second position, the other heating assembly is in contact with the other of the positive beads, and is powered on.

16. The atomizer of claim 15, wherein the two heating assemblies are configured for heating and atomizing oil of identical taste.

17. The atomizer of claim 15, wherein the fixing assembly comprises an upper holder, the upper holder is hermetically coupled to the mouthpiece assembly, the two heating assemblies each comprise an air tube, the upper holder defines two fixing holes therein, and the two air pipes are detachably coupled in the two fixing holes respectively.

18. The atomizer of claim 15, wherein each air pipe comprises a first part, a second part, and a middle part detachably interconnected between the first part and the second part, one end of the first part is detachably coupled to the fixing hole.

* * * * *